Figure 1:
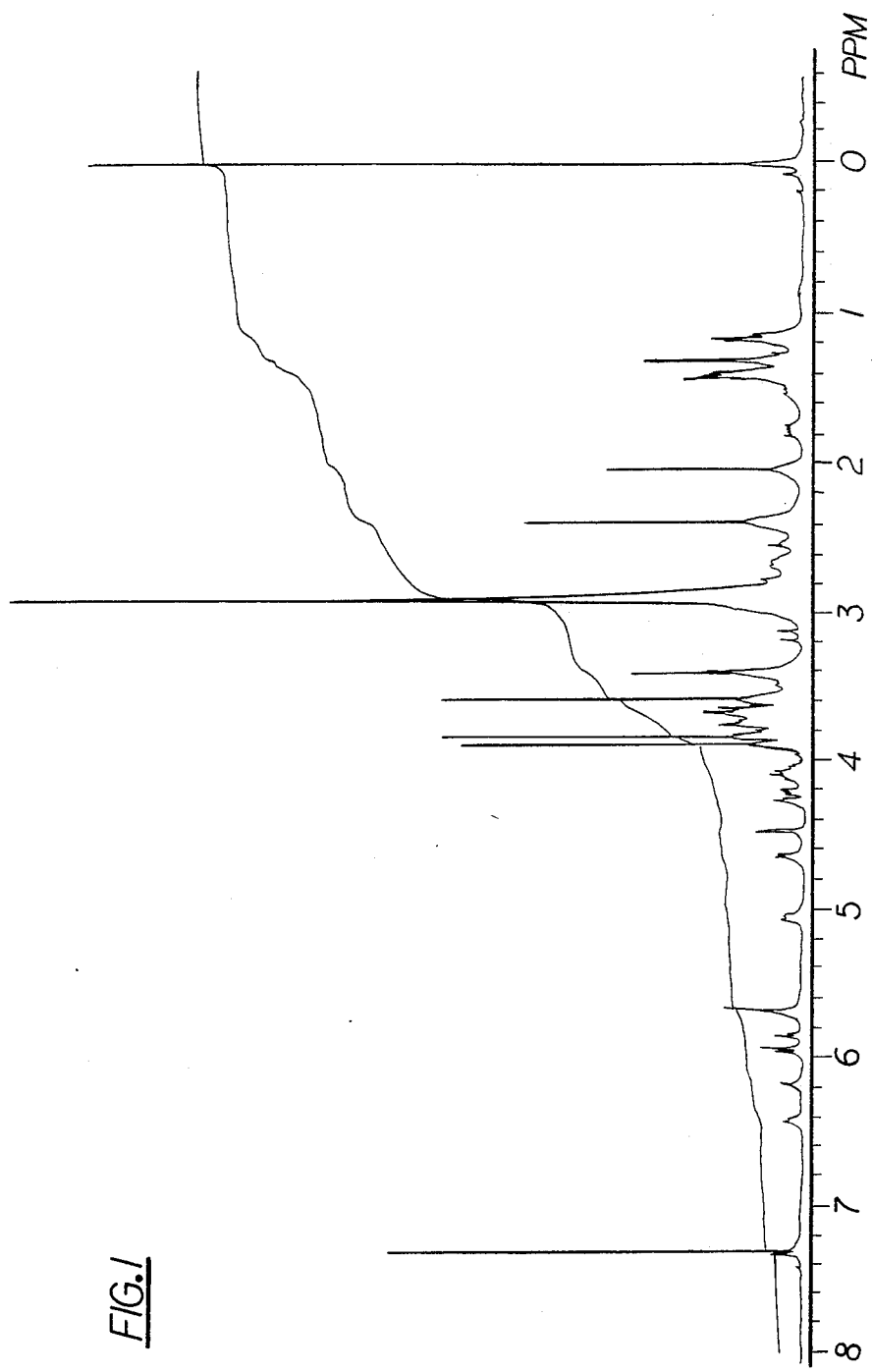

United States Patent [19]

Ellestad et al.

[11] Patent Number: 4,978,748

[45] Date of Patent: Dec. 18, 1990

[54] INTERMEDIATE AND PROCESS FOR PRODUCING THE ANTIBACTERIAL AND ANTITUMOR AGENTS LL-E33288ε-I AND LL-E33288EPSILON-BR

[75] Inventors: George A. Ellestad, Pearl River, N.Y.; William J. McGahren, Demarest, N.J.

[73] Assignee: American Cyanamid Company, Stamford, Conn.

[21] Appl. No.: 161,626

[22] Filed: Feb. 29, 1988

[51] Int. Cl.$^5$ .......................... C07H 5/00; C07H 15/00
[52] U.S. Cl. .................................. 536/17.5; 536/16.8; 536/16.9; 536/18.4; 536/122
[58] Field of Search .................... 536/16.8, 16.9, 17.5, 536/17.6, 18.4, 122, 18.1, 17.2

[56] References Cited

U.S. PATENT DOCUMENTS 4,837,206 6/1989 Golik .................................. 536/16.8

FOREIGN PATENT DOCUMENTS 0157203 10/1985 European Pat. Off. .
0182152 5/1986 European Pat. Off. .

OTHER PUBLICATIONS

Lee et al; J. Am. Chem. Soc. 109: 3464–3468 (1987).
Schreiber et al; J. Am. Chem. Soc. 110: 631–633 (1988).

Primary Examiner—Ronald W. Griffin
Assistant Examiner—Nancy S. Carson
Attorney, Agent, or Firm—Thomas S. Szatkowski

[57] ABSTRACT

Processes for producing antibacterial and antitumor agents designated LL-E33288ε-I and LL-E33288ε-Br using triphenylphosphine at ice bath temperature are disclosed. Novel intermediates prepared in the processes are also disclosed.

9 Claims, 1 Drawing Sheet

INTERMEDIATE AND PROCESS FOR PRODUCING THE ANTIBACTERIAL AND ANTITUMOR AGENTS LL-E33288ε-I AND LL-E33288EPSILON-BR

BACKGROUND OF THE INVENTION

The family of antibacterial and antitumor agents, known collectively as the LL-E33288 complex, are described and claimed in a series of related commonly-assigned U.S. patent applications, namely Ser. No. 672,031, filed Nov. 16, 1984 (now abandoned); Ser. No. 787,066, filed Oct. 17, 1985 (now abandoned); and Ser. No. 9,321, filed Jan. 30, 1987.

These applications describe the LL-E33288 complex, the components thereof, namely LL-E33288$\alpha_1$-Br, LL-E33288$\alpha_1$-I, LL-E33288$\alpha_2$-Br, LL-E33288$\alpha_2$-I, LL-E33288$\alpha_3$-Br, LL-E33288$\alpha_3$-I, LL-E33288$\alpha_4$-Br, LL-E33288$\beta_1$-Br, LL-E33288$\beta_1$-I, LL-E33288$\beta_2$-Br, LL-E33288$\beta_2$-I, LL-E33288$\gamma_1$-Br, LL-E33288$\gamma_1$-I, and LL-E33288$\delta_1$-I, and methods for their production by aerobic fermentation utilizing a new strain of *Micromonospora echinospora* ssp *calichensis* or natural or derived mutants thereof.

The antibacterial agents LL-E33288ε-I and LL-E33288ε-Br are described in commonly-assigned, co-pending Ser. No. 07/161,627, filed Feb. 29, 1988, together with methods for their production by aerobic fermentation of the above named microorganisms.

SUMMARY OF THE INVENTION

This invention is concerned with a synthetic process for producing LL-E33288ε-I and LL-E33288ε-Br from LLE33288$\gamma_1$-I and LL-E33288$\gamma_1$-Br and with intermediates developed during this process, called dethiomethy$\gamma_1$ or dimers, which have antitumor activity of their own.

These reactions are represented schematically below and proposed structures for LL-E33288ε-I and Br, LL-E33288$\gamma_1$-I and Br, LL-E33288$\delta_1$-I and the iodo and bromo dimers are given.

LL-E33288$\gamma_1$-I +
1

TRIPHENYLPHOSPHINE $\xrightarrow{\text{Dichloromethane}}{0°\text{ C.}}$

Dethiomethyl$\gamma_1$-I +
2

TRIPHENYLPHOSPHINE $\xrightarrow{\text{Methanol}}{D}$ LL-E33288$\epsilon_1$-I
3

This invention is also concerned with the dethiomethyl derivative of LL-E33288$\delta_1$-I which may be prepared by the following reaction sequence.

LL-E33288$\delta_1$-I +

TRIPHENYLPHOSPHINE $\xrightarrow{\text{Dichloromethane}}{0°\text{ C.}}$ Dethiomethyl$\delta_1$-I Additionally, the same reaction may be used to prepare dethiomethyl$\delta_1$-Br from LL-E33288$\delta_1$-Br.

In accordance with the above reaction scheme LL-E33288$\gamma_1$-I 1 is dissolved in dichloromethane, cooled in an ice bath and treated with a solution of triphenylphosphine in dichloromethane giving dethiomethyl$\gamma_1$-I 2, which is purified by reverse-phase, preparative high performance liquid chromatography using a column from Separations Technology, dissolved in methanol and treated with triphenylphosphine, with slight warming to produce LL-E33288ε-I.

The reaction of LL-E33288$\gamma_1$-Br using the above sequence produces dethiomethyl$\gamma_1$-Br and then LL-E33288ε-Br. Similarly, the same sequence may be used to convert dethiomethyl$\delta_1$-I to LL-E33288$\epsilon_1$-I and to convert dethiomethyl$\delta_1$-Br to LL-E33288$\epsilon_1$Br.

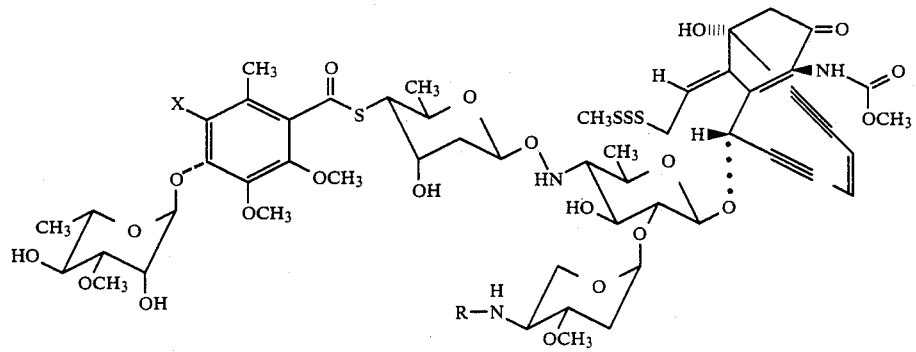

Proposed Structures for LL-E33288$\gamma_1$-I (X = I, R = CH$_2$CH$_3$)
LL-E33288$\gamma_1$-Br (X = Br, R = CH$_2$CH$_3$), and
LL-E33288$\delta_1$-I (X = I, R = CH$_3$)

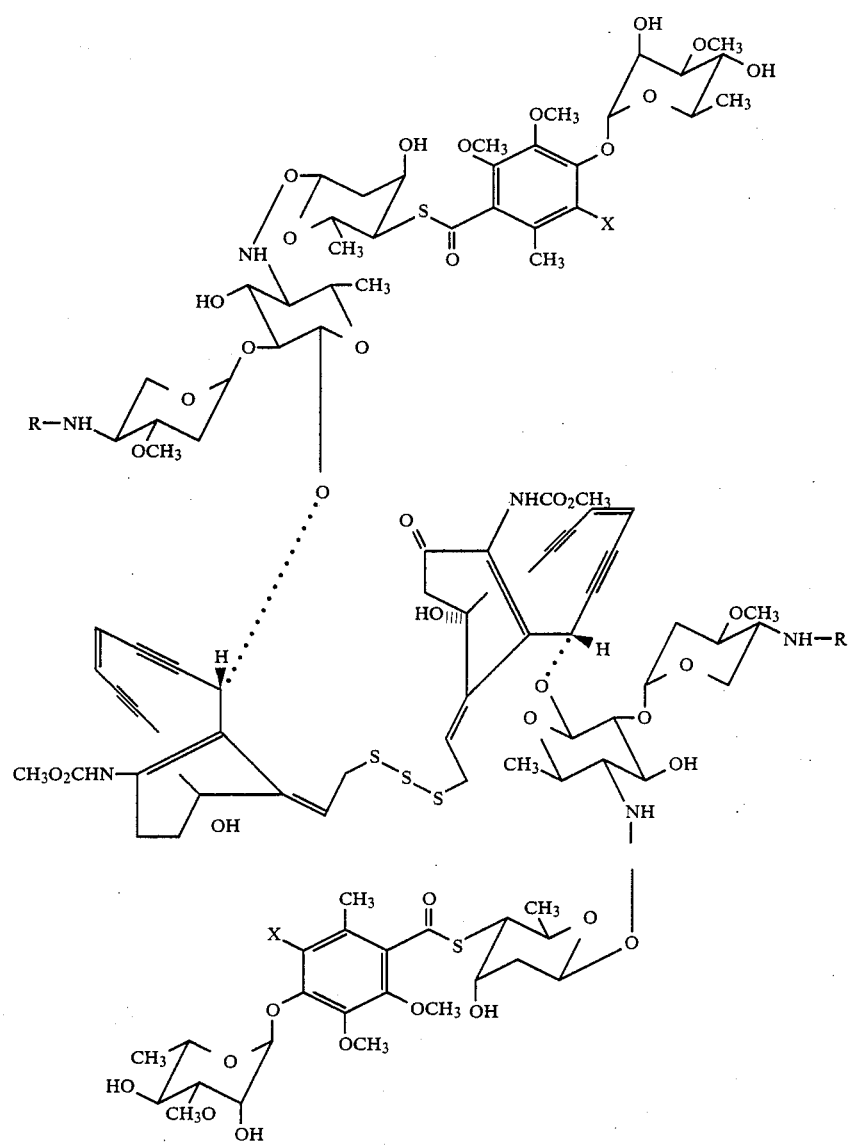
Dethiomethyl$\gamma_1$-I (X = I, R = CH$_2$CH$_3$)
Dethiomethyl$\gamma_1$-Br (X = Br, R = CH$_2$CH$_3$)
Dethiomethyl$\delta_1$-I (X = I, R = CH$_3$)
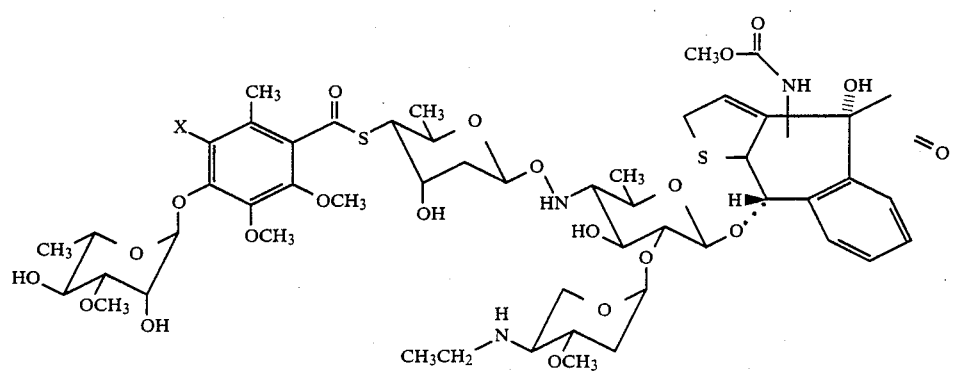
LL-E33288$\epsilon$-I (X = I)
LL-E33288$\epsilon$-Br (X = Br)

The physical-chemical characteristics of LL-E33288ε-I and LL-E33288ε-Br are given in commonly-assigned, copending application Ser. No. 07/161,627, filed Feb. 29, 1988. The physical-chemical characteristics of dethiomethyl$\gamma_1$-I are:

(a) Elemental analysis: C, 46.46; H, 5.80; N, 3.01; I, 9.10; and S, 5.74;
(b) Molecular formula: $C_{108}H_{142}N_6O_{42}I_2S_5$;
(c) Molecular weight: 2608.4 (FABMS); and
(d) a proton magnetic resonance spectrum as shown in FIG. I (300 MHz, $CDCl_3$).

The in vitro antibacterial activity of dethiomethyl$\gamma_1$-I was determined against a spectrum of gram-positive and gram-negative bacteria by a standard agar dilution method. Mueller-Hinton agar containing two-fold decreasing concentrations of the antibiotic were poured into petri plates. The agar surfaces were inoculated with 1 to $5 \times 10^4$ colony forming units of bacteria by means of a Steers replicating device. The lowest concentration of dethiomethyl$\gamma_1$-I that inhibited growth of a bacterial strain after about 18 hours growth at 35° C. was recorded as the minimal inhibitory concentration (MIC) for that strain. The results appear in Table I.

TABLE I

In vitro Antibacterial Activity of dethiomethyl$\gamma_1$-I

| Organism | Minimal Inhibitory Concentration (μg/ml) |
|---|---|
| Escherichia coli CMC 84-11 | 4 |
| Escherichia coli No. 311-(MP) | 4 |
| Escherichia coli ATCC 25922 | 2 |
| Klebsiella pneumoniae CMC 84-5 | 8 |
| Klebsiella pneumoniae AD (MP) | 2 |
| Enterobacter cloacae CMC 84-4 | 8 |
| Enterobacter aerogenes IO 83-44 | 8 |
| Serratia marcescens CMC 83-27 | 4 |
| Serratia marcescens F 35 (MP) | 4 |
| Morganella morganii IO 83-18 | 4 |
| Providencia stuartii CMC 83-82 | 8 |
| Citrobacter diversus K 82-24 | 4 |
| Citrobacter freundii IO 83-13 | 2 |
| Acinetobacter sp CMC 83-89 | 4 |
| Acinetobacter sp IO 83-49 | 4 |
| Pseudomonas aeruginosa 12-4-4 (MP) | 4 |
| Pseudomonas aeruginosa ATCC 27853 | 4 |
| Staphylococcus aureus Smith | $\leq 4 \times 10^{-6}$ |
| Staphylococcus aureus SSC 82-21 | $3 \times 10^{-5}$ |
| Staphylococcus aureus ATCC 25923 | $4 \times 10^{-3}$ |
| Staphylococcus aureus SSC 82-20 | $2.5 \times 10^{-4}$ |
| Staphylococcus aureus SSC 82-23 | $6 \times 10^{-5}$ |
| Staphylococcus aureus SSC 82-24 | $\leq 4 \times 10^{-6}$ |
| Staphylococcus aureus SSC 82-54 | $3 \times 10^{-5}$ |
| Staphylococcus epidermidis CMC 83-133 | $1.2 \times 10^{-4}$ |
| Staphylococcus epidermidis ATCC 12228 | $1 \times 10^{-3}$ |
| Streptococcus faecalis ATCC 29212 | $1.5 \times 10^{-2}$ |
| Streptococcus faecalis VGH 84-65 | $1.5 \times 10^{-2}$ |
| Streptococcus faecalis CMC 83-53 | $2.5 \times 10^{-1}$ |
| Streotococcus faecalis UCI 85-20 | $1.5 \times 10^{-2}$ |
| Streptococcus faecalis IO 83-28 | $1.5 \times 10^{-2}$ |

Certain in vivo testing systems and protocols have been developed by the National Cancer Institute for testing compounds to determine their suitability as antineoplastic agents. These have been reported in "Cancer Chemotherapy Reports", Part III, Volume 3, No. 2 (1972), Geran, et al. These protocols have established standardized screening tests which are generally followed in the field of testing for antitumor agents. Of these systems, lymphocytic leukemia P388 is particularly significant to the present invention. This neoplasm is utilized for testing as transplantable tumors in mice. Significant antitumor activity shown in this protocol by a percentage increase of mean survival times of the treated(T) animals over the control(C) animals is indicative of similar results in human leukemias and solid tumors.

Lymphocytic Leukemia P388 Test

The animals used were BDF1 mice, all of one sex, weighing a minimum of 17 g and all within a 3 g weight range. There were 5 or 6 mice per test group. The tumor transplant was by intraperitoneal injection of 0.5 ml of dilute ascitic fluid containing $10^6$ cells of lymphocytic leukemia P388. Dethiomethyl$\gamma_1$-I was administered intraperitoneally on days 1, 5 and 9 (relative to tumor inoculation) at the indicated doses. The mice were weighed and survivors recorded on a regular basis for 30 days. The median survival time and the ratio of survival time for treated(T)/control(C) animals were calculated. The results appear in Table II.

If $T/C \times 100$ (%) is 125 or over, the tested compound is considered to have significant anti-tumor activity.

TABLE II

Lymphocytic Leukemia P388 Test

| Compound | Dose (mg/kg) | Median Survival (Days) | T/C × 100 (%) |
|---|---|---|---|
| Dethiomethyl$\gamma_1$-I | 0.025 | 23.5 | 235 |
|  | 0.0125 | 22 | 220 |
|  | 0.0062 | 19.5 | 195 |
|  | 0.0031 | 18.5 | 185 |
|  | 0.00155 | 16 | 160 |
|  | 0.008 | 13 | 130 |
|  | 0.0004 | 12.5 | 125 |
| Control | — | 10 | — |
| Positive Control (Novantrone)* | 1.6 | 27 | 270 |
|  | 0.8 | >30 | >300 |
|  | 0.4 | 21.5 | 215 |

*1,4-bis[2-(2-hydroxy-ethylamino)ethylamino]-5,8-dihydroxyanthraquinone dihydrochloride, Lederle Laboratories, Pearl River, New York.

The invention is further illustrated by the Examples set forth below which are not intended to limit the invention.

EXAMPLE 1

Preparation of Dethiomethyl$\gamma_1$-I

One gram of LL-E33288$\gamma_1$-I in 50 ml of dichloromethane was cooled in an ice bath and treated with 293 mg of triphenylphosphine in 2 ml of dichloromethane. After stirring for 2 hours at ice bath temperature, the solution was allowed to warm to room temperature and the particulate dethiomethyl$\gamma_1$-I collected. This product was purified by preparative HPLC using a 1×14 inch Separations Technology column packed with $C_{18}$ reverse phase support (25μ) with the solvent system acetonitrile:0.2M ammonium acetate (48:52). Fractions containing dethiomethyl$\gamma_1$-I were identified using thin layer chromatography ("TLC"). The TLC plates were placed in ethyl acetate saturated with a buffer of 0.2M dipotassium hydrogen phosphate containing 10% isopropanol. The plates were then ultraviolet quenched to identify the fractions of interest (fractions 5 and 6). Fractions 5 and 6 were combined, the acetonitrile removed in vacuo and the resultant cloudy solution extracted with ethyl acetate. The ethyl acetate solution was washed with water, dried, concentrated to a small volume and added dropwise to 100 ml of hexane with stirring. The precipitate was collected and dried, giving 168 mg of dethiomethyl$\gamma_1$-I.

EXAMPLE 2

Conversion of Dethiomethyl$\gamma_1$-I to LL-E33288$\epsilon$-I

To a solution of 42 mg of dethiomethyl$\gamma_1$-I in 10 ml of methanol was added 10 mg of triphenylphosphine. The mixture was warmed and then stirred for 16 hours at room temperature. A 12 mg portion of triphenylphosphine was added followed by warming at 40°–50° C. for one hour. The resulting LL-E33288$\epsilon$-I was purified by preparative TLC using Whatman 1000m silica gel plates. Extraction of the LL-E33288$\epsilon$-I zone with ethyl acetate gave 4 mg of pure product.

We claim:

1. A process for producing LL-E33288$\epsilon$-I, which comprises reacting LL-33288$\gamma_1$-I having the structure:

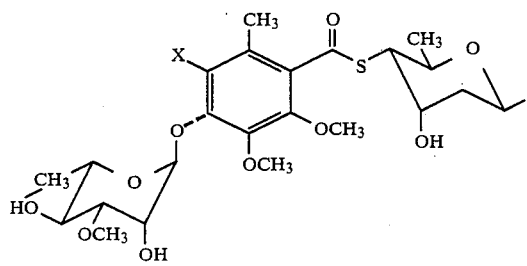

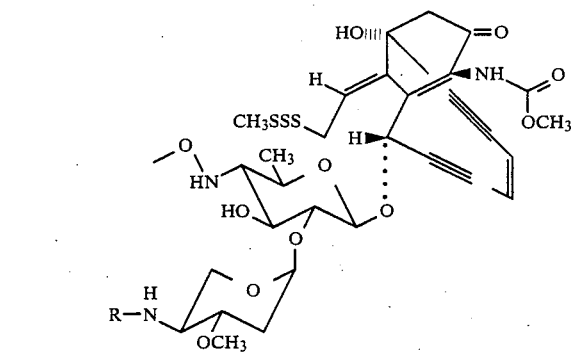

wherein X=I and R=CH$_2$CH$_3$
with triphenylphosphine is dichloromethane at ice bath temperature, following by warming to room temperature, collecting the so formed dethiomethyl$\gamma_1$-I, having the structure:

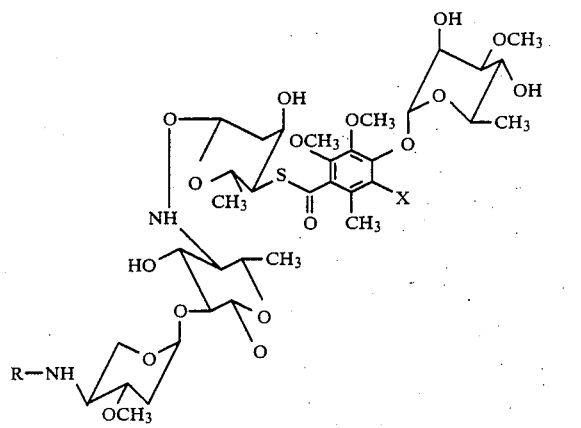

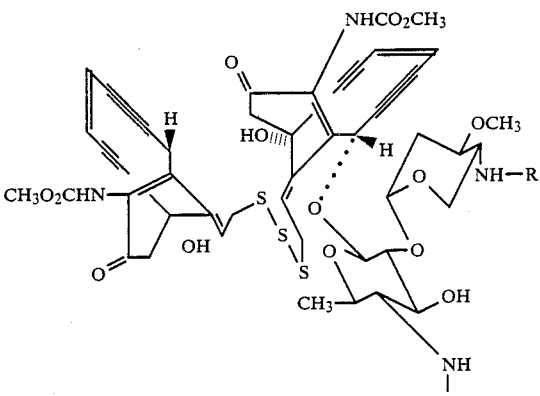

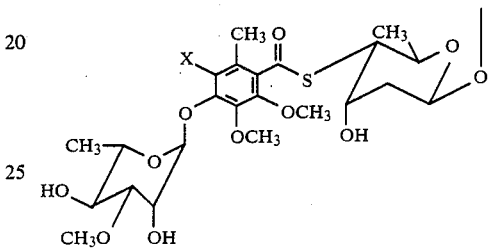

wherein X=I and R=CH$_2$CH$_3$
reacting the dethiomethyl$\gamma$-I with triphenylphosphine in methanol with slight warming and collection of the so formed LL-E33328$\epsilon$-I having the structure:

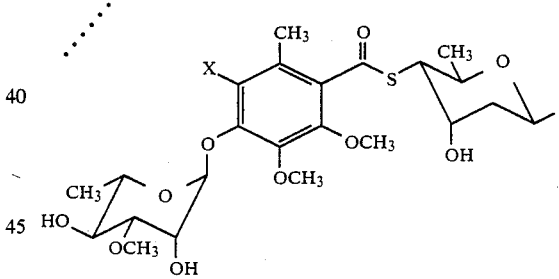

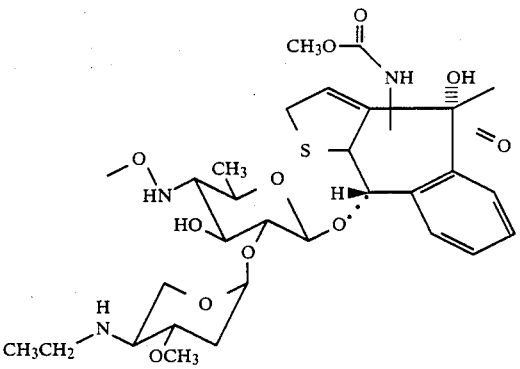

wherein X=I.

2. A process for producing LL-E33288$\epsilon$-Br, which comprises reacting LL-E33288$\gamma_1$-Br having the structure:

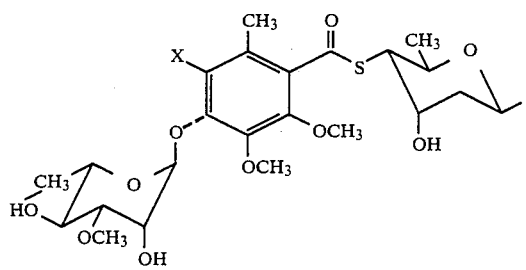

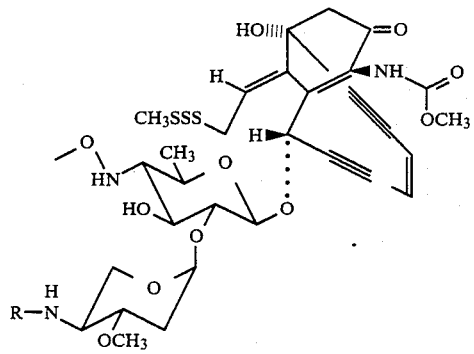

wherein X=Br and R=CH₂CH₃ with triphenylphosphine in dichloromethane at ice bath temperature, followed by warming to room temperature, collecting the so formed dethiomethylγ₁-Br having the structure:

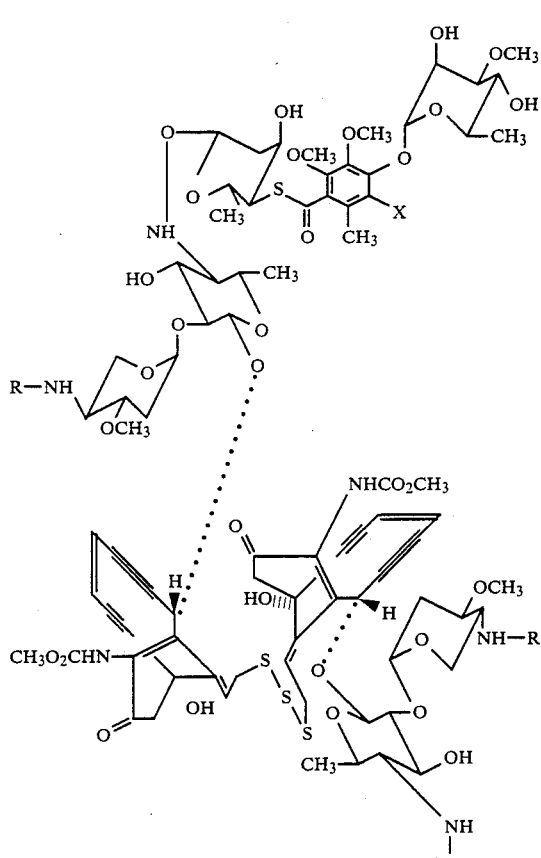

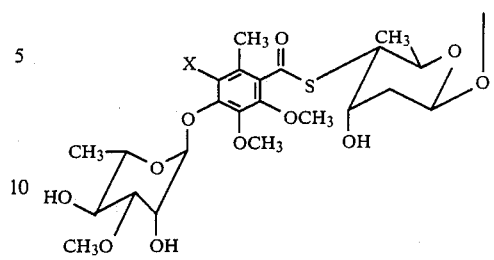

wherein X=Br and R=CH₂CH₃ reacting the dethiomethylγ₁-Br with triphenylphosphine in methanol with slight warming and collection of the so formed LL-E33288ε-Br having the structure:

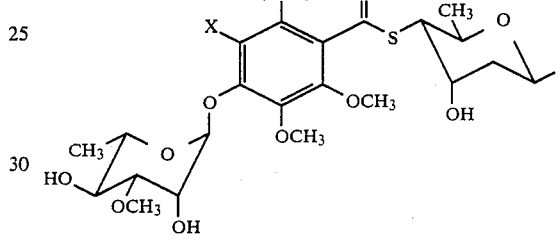

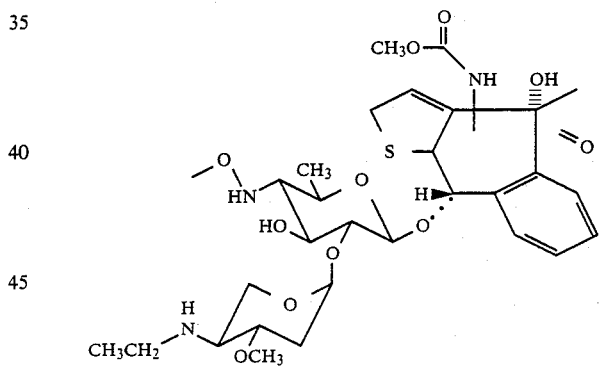

wherein X=Br.

3. A process for producing LL-E33288ε-I which comprises reacting LL-E33288δ₁-I having the structure:

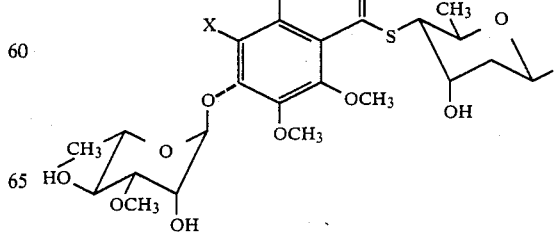

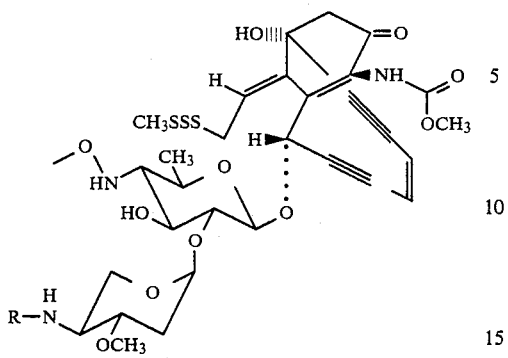

wherein X=I and R=CH₃,
with triphenylphosphine in dichloromethane at ice bath temperature, followed by warming to room temperature, collecting the so formed dethiomethylδ₁-I, having the structure:

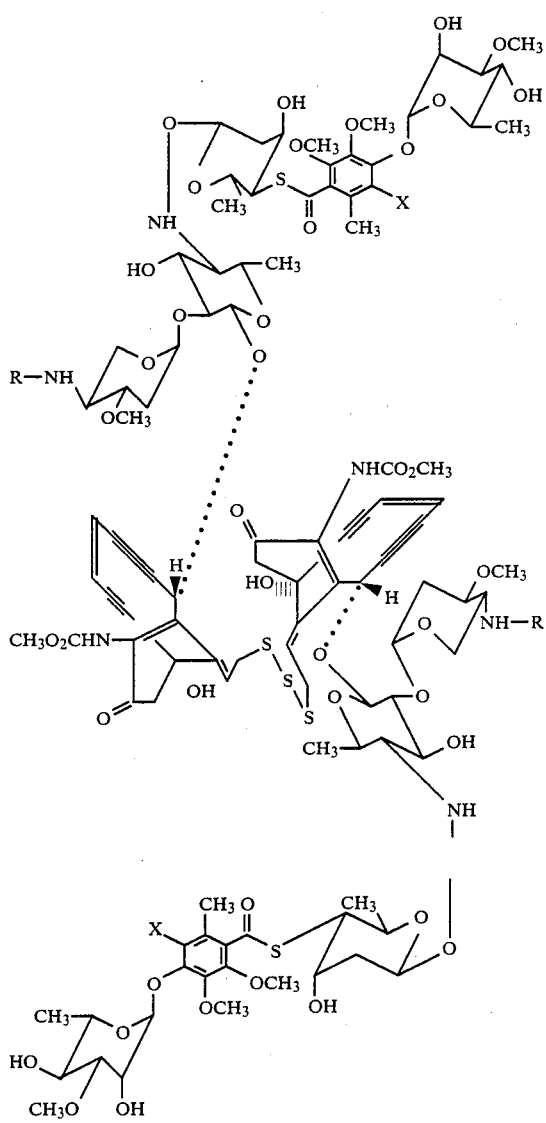

wherein X=I and R=CH₃ reacting the dethiomethylδ₁-I with triphenylphosphine in methanol with slight warming and collection of the so formed LL-E33288ε-I having the structure:

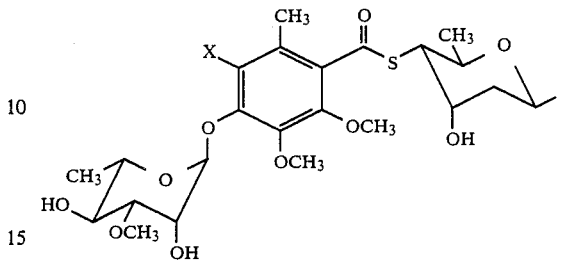

wherein X=I.

4. A process for producing LL-E33288ε-Br, which comprises reacting LL-E33288δ₁-Br having the structure:

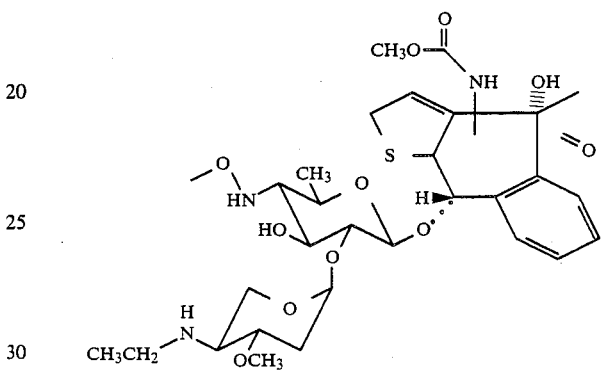

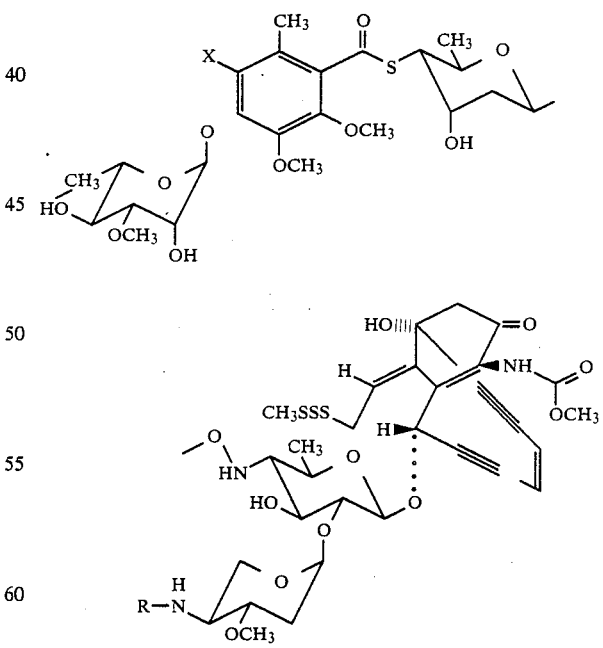

wherein X=Br and R=CH₃
with triphenylphosphine in dichloromethane at ice bath temperature, followed by warming to room temperature, collecting the so formed dethiomethylδ₁-Br, having the structure:

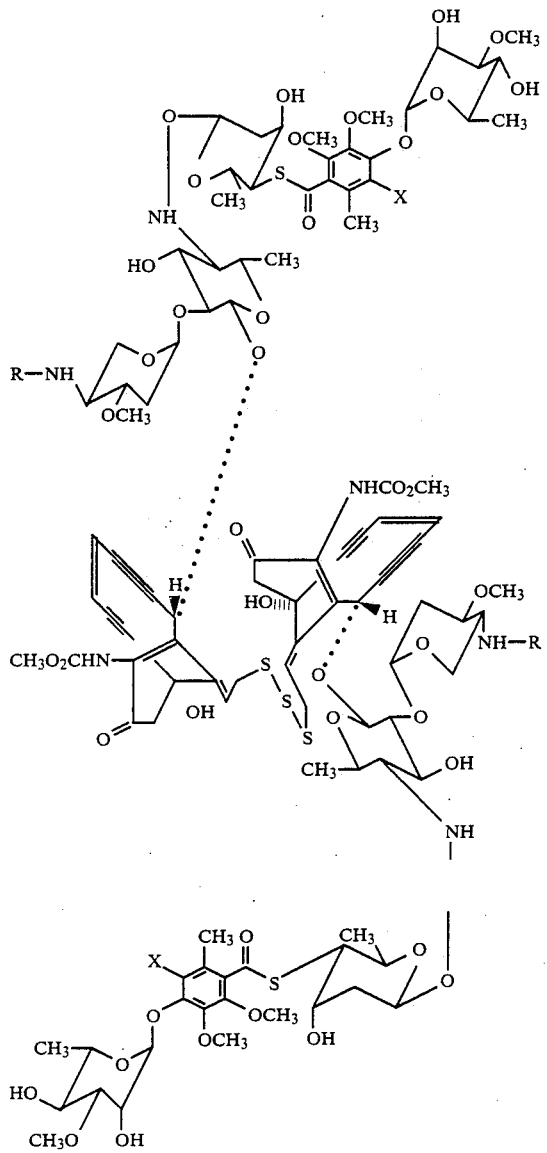

wherein X=Br and R=CH3 reacting the dethiomethylδ1-Br with triphenylphosphine in methanol with slight warming and collection of the so formed LL-E33288ε-Br having the structure:

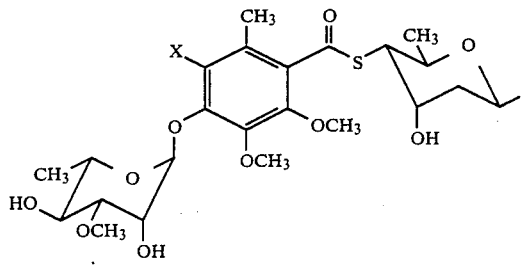

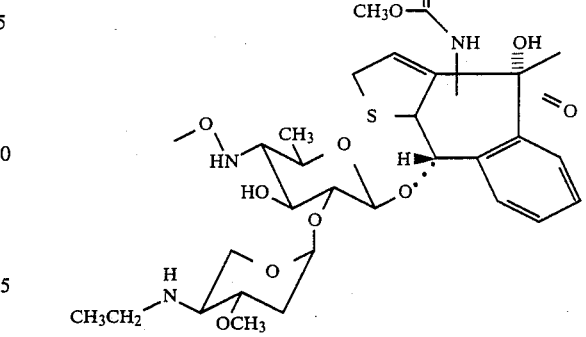

wherein X=Br.

5. The compound dethiomethylγ1-I which has:

(a) a molecular formula: $C_{108}H_{142}N_6O_{42}I_2S_5$;

(b) an elemental analysis: C, 46.46; H, 5.80; N, 3.01; I, 9.10; and S, 5.74;

(c) a molecular weight: 2608.4 (FABMS);

(d) a proton magnetic resonance spectrum as shown in FIG. I; and (e) a structure

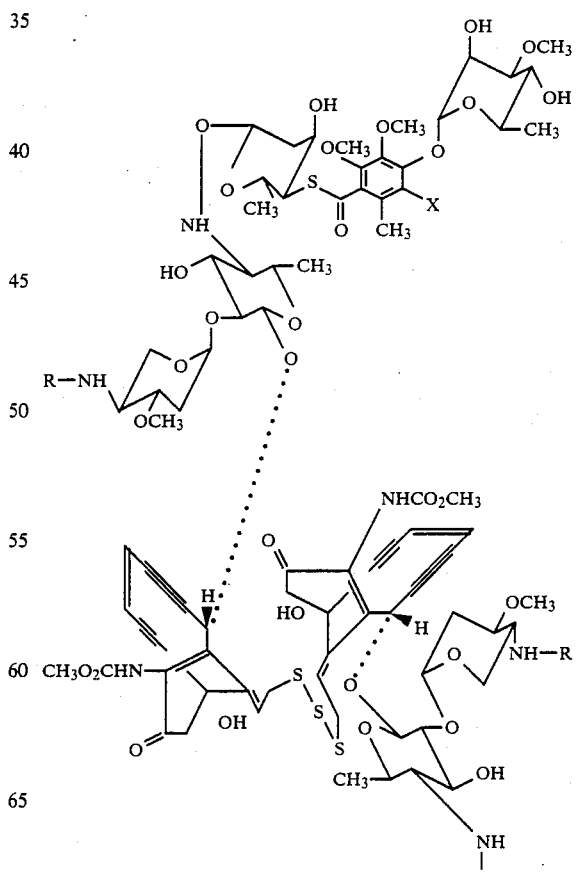

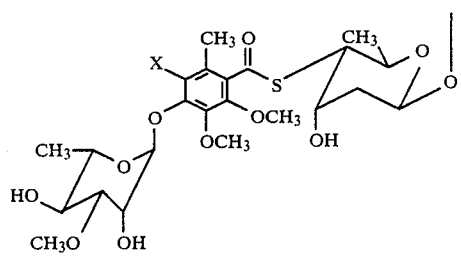

wherein X=I and R=CH$_2$CH$_3$.

6. The compound dethiomethylγ$_1$-I having the structure:

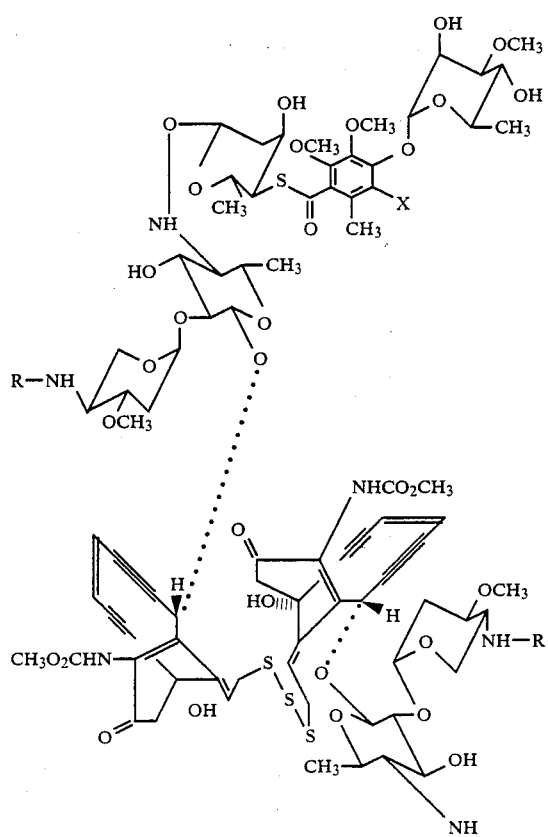

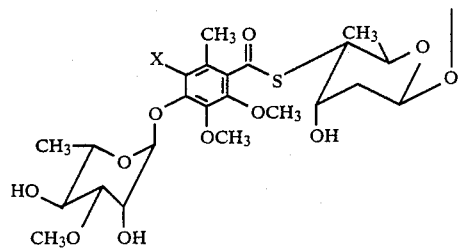

wherein X=I and R=CH$_2$CH$_3$
when produced by the reaction of LL-33288γ$_1$-I having the structure:

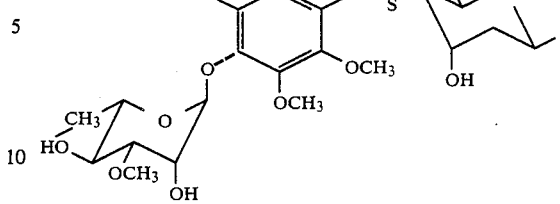

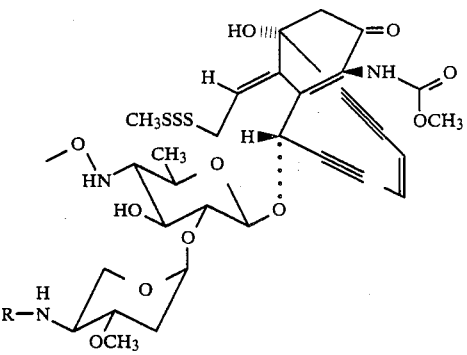

wherein X=I and R=CH$_2$CH$_3$
with triphenylphosphine in dichloromethane at ice bath temperature, followed by warming to room temperature.

7. The compound dethiomethylγ$_1$-Br having the structure:

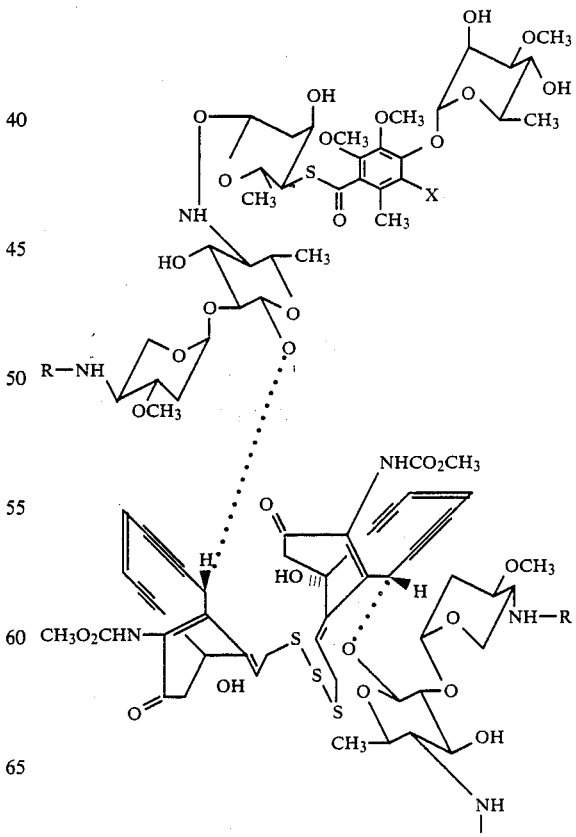

-continued

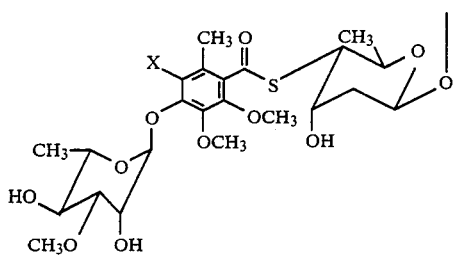

wherein X=Br and R=CH$_2$CH$_3$
when produced by the reaction of LL-E33288δ-Br having the structure:

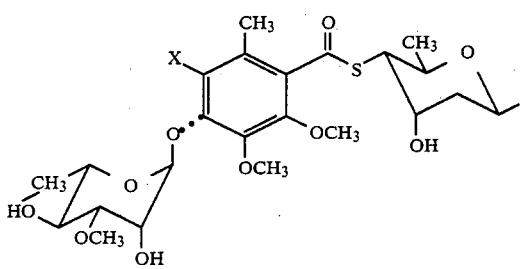

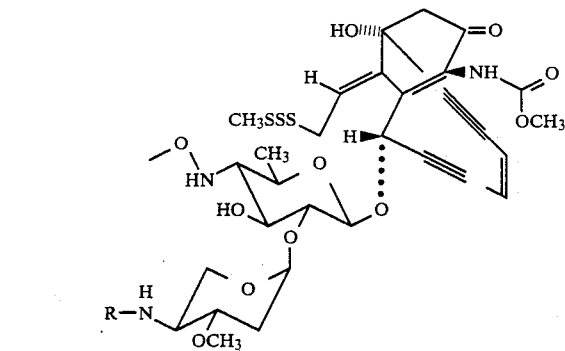

wherein X=Br and R=CH$_2$CH$_3$
with triphenylphosphine in dichloromethane at ice bath temperature, followed by warming to room temperature.

8. The compound dethiomethylδ$_1$-I having the structure:

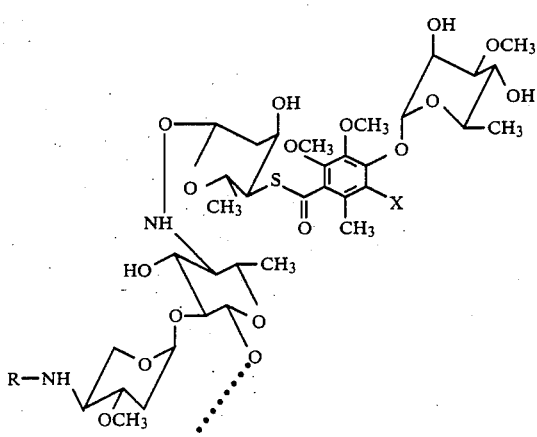

-continued

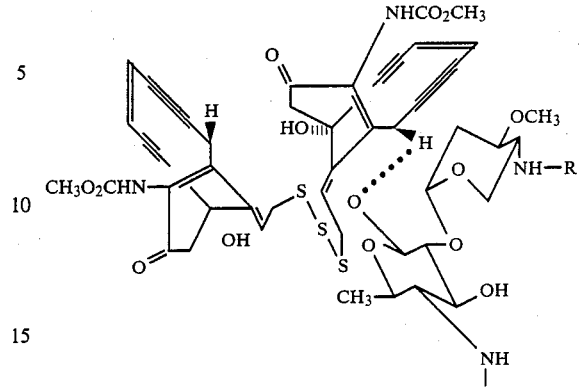

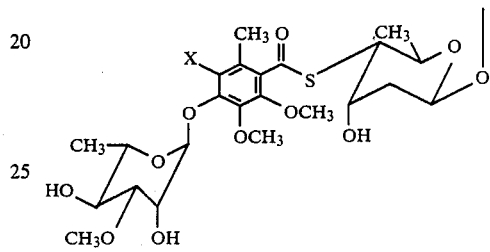

wherein X=I and R=CH$_3$
when produced by the reaction of LL-33288δ$_1$-I having the structure:

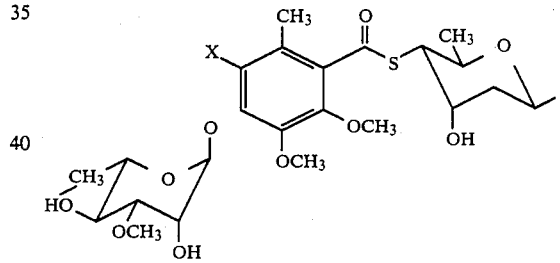

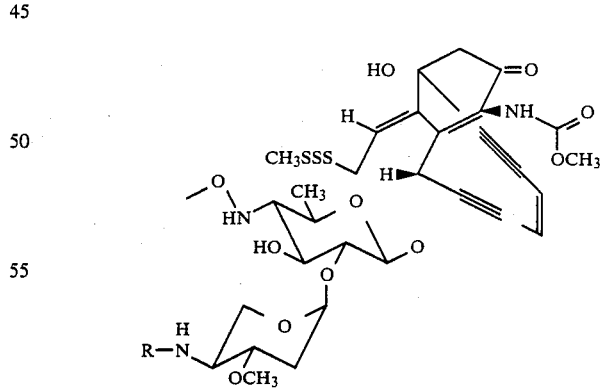

wherein X=I and R=CH$_3$
with triphenylphosphine in dichloromethane at ice bath temperature, followed by warming to room temperature.

9. The compound dethiomethylδ$_1$-Br having the structure:

-continued
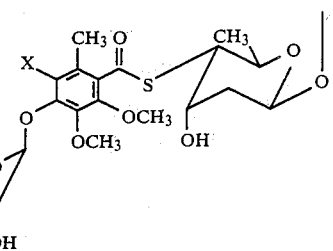
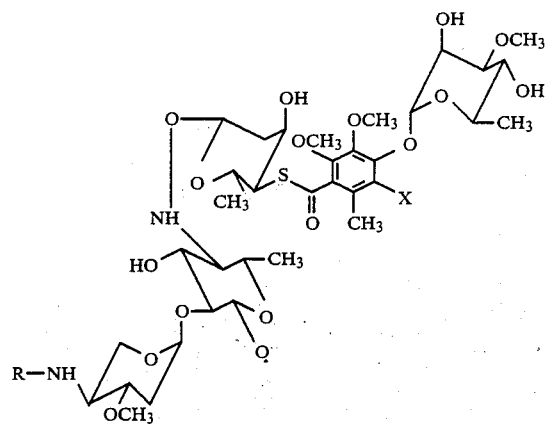
wherein X=Br and R=CH$_3$
when produced by the reaction of LL-E33288δ-Br having the structure:
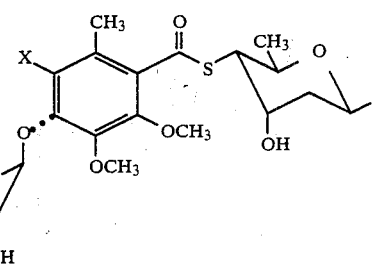
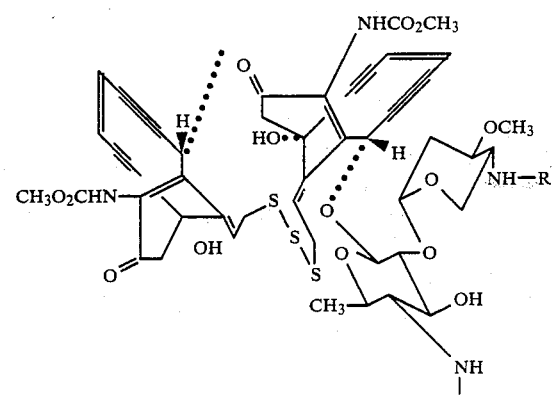
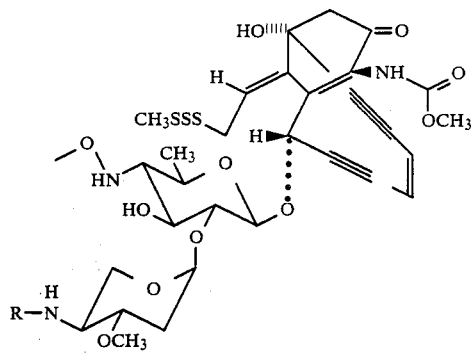
wherein X=Br and R=CH$_3$
with triphenylphosphine in dichloromethane at ice bath temperature, followed by warming to room temperature.
* * * * *